United States Patent
Lee et al.

(10) Patent No.: US 7,695,893 B2
(45) Date of Patent: Apr. 13, 2010

(54) PHOTO-SENSITIVE COMPOUND AND PHOTORESIST COMPOSITION INCLUDING THE SAME

(75) Inventors: Jae-Woo Lee, Bucheon-Si (KR);
Jung-Youl Lee, Anyang-Si (KR);
Jeong-Sik Kim, Yeongiu-Si (KR);
Eu-Jean Jang, Hwaseong-Si (KR);
Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 0 days.

(21) Appl. No.: 12/134,840

(22) Filed: Jun. 6, 2008

(65) Prior Publication Data
US 2008/0305430 A1 Dec. 11, 2008

(30) Foreign Application Priority Data
Jun. 8, 2007 (KR) .................. 10-2007-0056203

(51) Int. Cl.
*G03F 7/038* (2006.01)
*G03F 7/20* (2006.01)
*G03F 7/30* (2006.01)

(52) U.S. Cl. .................. 430/270.1; 430/325; 430/330; 562/488; 562/489

(58) Field of Classification Search ............ None
See application file for complete search history.

(56) References Cited

FOREIGN PATENT DOCUMENTS

JP 2005-314813 * 11/2005

OTHER PUBLICATIONS

JPO English abstract for JP2005-314813.*
Machine-assisted English translation for JP2005-314813, provided by JPO.*

* cited by examiner

*Primary Examiner*—Sin J. Lee
(74) *Attorney, Agent, or Firm*—Birch, Stewart, Kolasch & Birch, LLP

(57) ABSTRACT

Disclosed are a photo-sensitive compound and a photoresist composition containing the same, for forming ultra-fine photoresist patterns. The photo-sensitive compound is resented by following Formula 1,

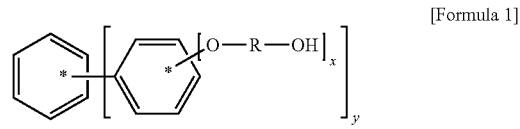

[Formula 1]

wherein x is an integer of 1 to 5, y is an integer of 2 to 6, R is a $C_2 \sim C_{20}$ hydrocarbon group. The photoresist composition comprises 1~85 weight % of a photo-sensitive compound represented by following Formula 1, 1~55 weight % of a compound which reacts with a hydroxyl group (—OH) of the compound represented by Formula 1 to combine with the photo-sensitive compound represented by Formula 1; 1~15 weight % of a photo-acid generator; and 12~97 weight % of an organic solvent.

7 Claims, 1 Drawing Sheet

[FIG. 1]
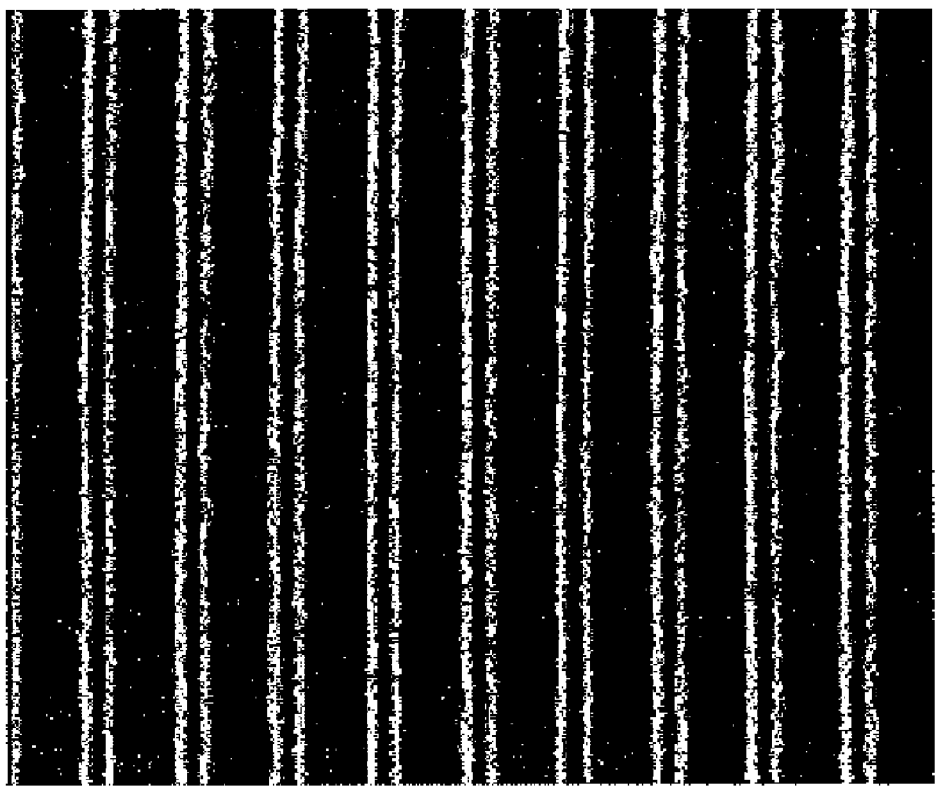

PHOTO-SENSITIVE COMPOUND AND PHOTORESIST COMPOSITION INCLUDING THE SAME

This application claims the priority benefit of Korean Patent Application No. 10-2007-0056203 filed on Jun. 8, 2007. All disclosure of the Korean Patent application is incorporated herein by reference.

FIELD OF THE INVENTION

This invention relates to a photo-sensitive compound and a photoresist composition including the same, and more specifically to a photo-sensitive compound by which an ultra-fine circuit pattern can be formed and a photoresist composition including the same.

BACKGROUNDS OF THE INVENTION

The photolithography is a process used to form a circuit pattern of a semiconductor chip or a display element from a semiconductor wafer or a glass for the display element. The photoresist composition is the most essential materials to the photolithography process. So, recently, as the patterns for semiconductor devices and the display elements are finer, the need for the photoresist composition having high resolution is more increased.

Conventional acid-amplified photoresist composition includes a polymer resin, a photo-acid generator (PAG) and a base additive. Since the conventional photoresist composition includes the polymer resin as a main component, it has excellent mechanical properties such as processiblity, coating stability, etching resistance and can be easily removed after the succeeding process including an etching process, an ion implantation process etc. It has been known that the size of the polymer resin determines the critical resolution of the photoresist composition. That is, when the size of the polymer resin of the photoresist composition is larger than the pattern to be formed, it is difficult to form a fine pattern in a desired resolution. Also, since the polymer resin is an aggregate of polymer chains having various structures and sizes, i.e. non-uniform mixture, it is more difficult to form a fine pattern using the polymer resin. Accordingly, it has been known that by using the conventional photoresist composition, manufacturing a fine-structured semiconductor device having a design rule of less than 65 nm is difficult. For overcoming the above mentioned problems, a study of new photoresist materials which can substitute for the polymer resin is demanded.

SUMMARY OF THE INVENTION

Therefore, it is an object of the present invention to provide a photo-sensitive compound whose size is smaller than conventional polymer and which has well-defined (uniform) structure, and a photoresist composition including the same. It is another object of the present invention to provide a photo-sensitive compound having a good coating uniformity and a high resolution, and capable of reducing a line edge roughness (LER), and a photoresist composition including the same. It is still another object to provide a photo-sensitive compound having an excellent developing property and dry etch resistance, and a photoresist composition including the same.

To accomplish these objects, the present invention provides a photo-sensitive compound having a structure of Formula 1.

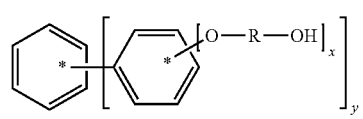

[Formula 1]

In Formula 1, x is an integer of 1 to 5, y is an integer of 2 to 6 and R is a $C_2$~$C_{20}$ hydrocarbon group.

Also, the present invention provides a photoresist composition including 1~85 weight % of the photo-sensitive compound of the Formula 1, 1~55 weight % of a compound which reacts with hydroxy group (—OH) in the compound represented by Formula 1 so as to combine with the photo-sensitive compound represented by Formula 1, 1~15 weight % of a PAG, and 12~97 weight % of an organic solvent. Here, preferably, the compound which combines with the photo-sensitive compound represented by Formula 1 contains

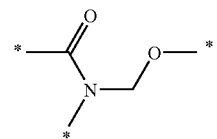

(* indicates a bonding part.).

BRIEF DESCRIPTION OF THE DRAWINGS

FIG. 1 shows an electron microphotograph of the photoresist pattern formed by using a photoresist composition according to one embodiment of the present invention.

DETAILED DESCRIPTION OF THE INVENTION

A more complete appreciation of the invention, and many of the attendant advantages thereof, will be better appreciated by reference to the following detailed description.

The photo-sensitive compound of the present invention, even under an acid catalyst, combines with a compound reacting with a hydroxy group (—OH) and has variable solubility with respect to the developer. The photo-sensitive compound of the present invention has a structure of following Formula 1.

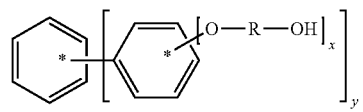

[Formula 1]

In Formula 1, x is an integer of 1 to 5, preferably 1, 2 or 3. y is an integer of 2 to 6, preferably 3. R is a substituted or non-substituted $C_2$~$C_{20}$ hydrocarbon group. For example R may be substituted with carbonyl, phenyl, sulfonyl or fluoroalkyl group or may have 0 to 8 hetero-atoms, preferably 1-8 hetero-atoms. Preferably R is a substituted or non-substituted $C_2$~$C_{20}$ chain or ring aliphatic hydrocarbon group or substituted or non-substituted $C_2$~$C_{20}$ chain or ring aromatic hydrocarbon group.

The representative examples of the photo-sensitive compound represented by Formula 1 are as follows.

[Formula 1a]
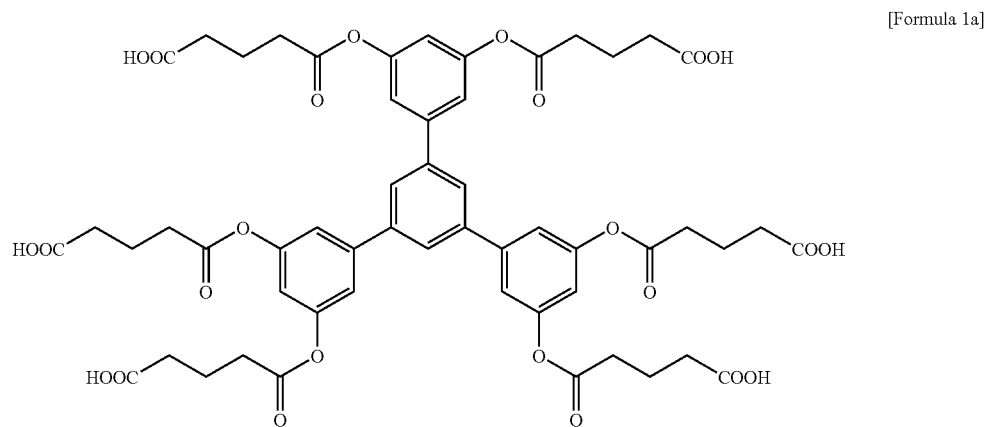
[Formula 1b]
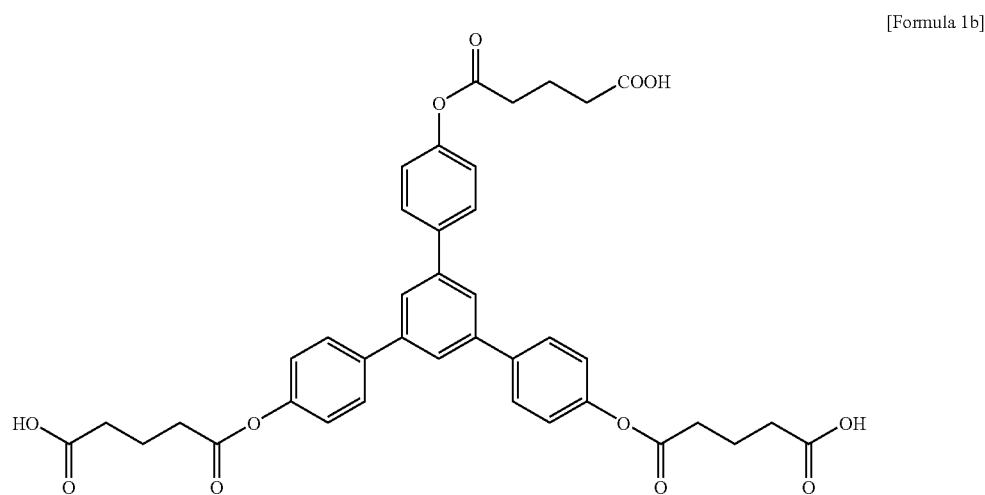
[Formula 1c]
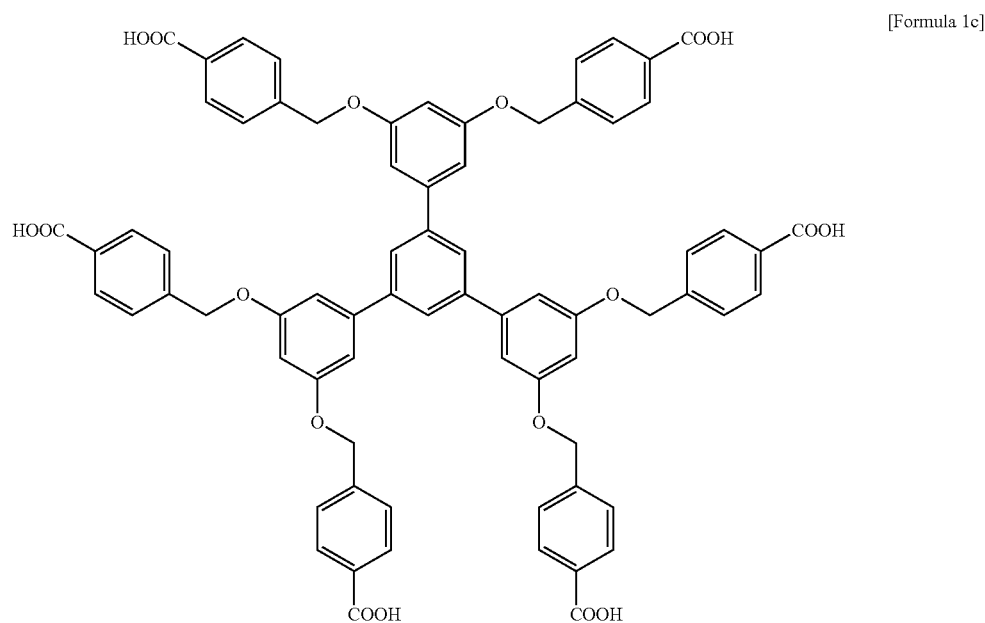

A compound which reacts with a hydroxyl group (—OH) of the compound represented by Formula 1, preferably carboxyl group (—COOH), to combine with the photo-sensitive compound represented by Formula 1, under the acid catalyst, includes a compound containing

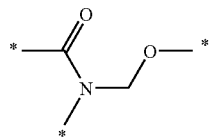

(* indicates the bonding part.). Preferably, compounds represented by Formula 2, Formula 3a~3c and Formula 4 can be used independently or by mixing them.

[Formula 2]

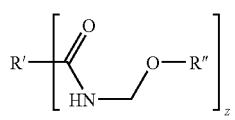

In Formula 2, z is an integer of 1 to 20. R' and R" are independently substituted or non-substituted $C_1$~$C_{30}$ hydrocarbon group. R' and R" may contain 0 to 5 hetero-atoms, preferably 1-5 hetero-atoms. Preferably, R' and R" are substituted or non-substituted $C_2$~$C_{30}$ chain or ring aliphatic hydrocarbon group or substituted or non-substituted $C_2$~$C_{30}$ chain or ring aromatic hydrocarbon group.

Representative examples of the photo-sensitive compound represented by

Formula 2 include (Formula 2a)

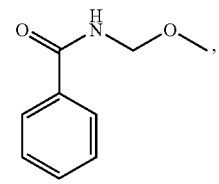

(Formula 2b)

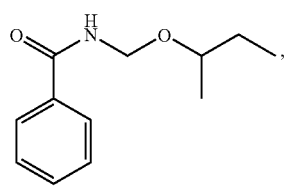

(Formula 2c)

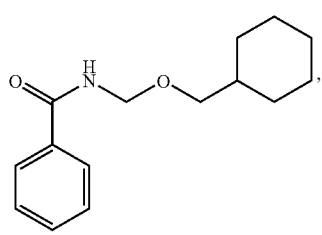

-continued (Formula 2d)

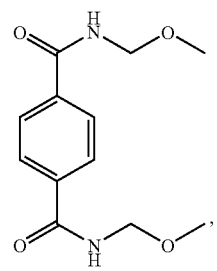

(Formula 2e)

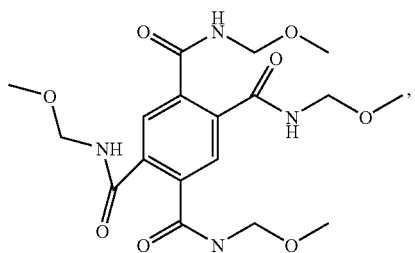

(Formula 2f)

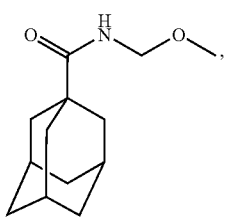

(Formula 2g)

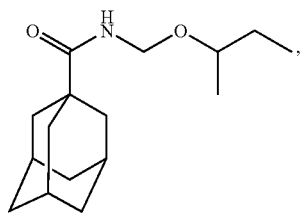

(Formula 2h)

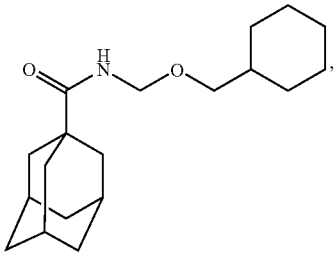

(Formula 2i)

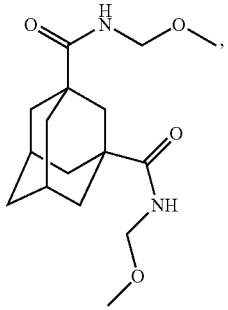

-continued (Formula 2j)
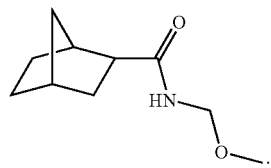

[Formula 3a]
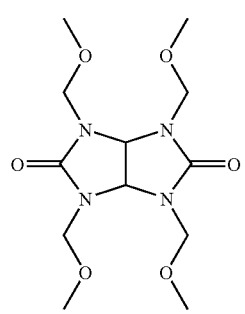

[Formula 3b]
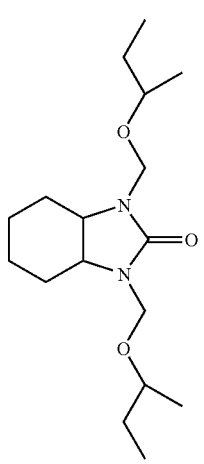

[Formula 3c]
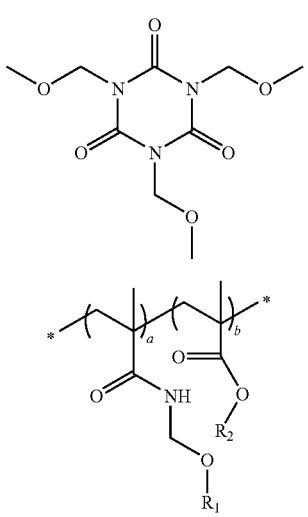

[Formula 4]

In Formula 4, a and b are mole % of respective repeating unit with respect to the total repeating unit composing the polymer represented by Formula 4. a and b are 1 to 99 mole % and 1 to 99 mole %, respectively. Each of $R_1$ and $R_2$ is the same to R' as defined in Formula 2. Preferably, the weight-average molecular weight (Mw) of the polymer represented by Formula 4 is 100 to 100,000. Example of such a polymer includes a polymer represented by following Formula 4a (Mw: 4,200, polydispersity index (PDI): 1.68).

[Formula 4a]
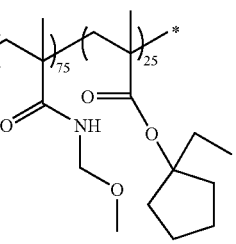

The photo-sensitive compound represented by Formula 1 according to the present invention, can be synthesized by a condensation reaction of acetophenone derivatives as described in following Reaction 1. The photo-sensitive compound represented by Formula 2 may be prepared by a nucleophilic substitution of amide derivatives or by conventionally polymerizing monomers composing the polymer. In polymerization, a conventional polymerization initiator such as azobis(isobutyronitrile) (AIBN) can be used. In following reaction 1, R is H or $C_1$~$C_{20}$ chain or ring aliphatic hydrocarbon group or $C_1$~$C_{20}$ chain or ring aromatic hydrocarbon group, and n is an integer of 1 to 5.

[Reaction 1]
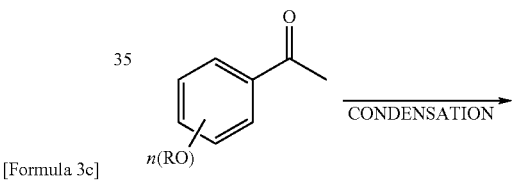
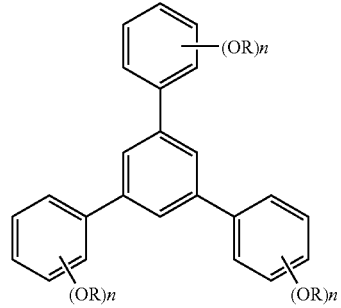

The photo-sensitive compound according to the present invention is subjected to a cross linking reaction at an exposure part of the photoresist under an acid catalyst, as shown in following Reaction 2 so that the solubility of the photo-sensitive compound is varied with respect to the developer.

[Reaction 2]
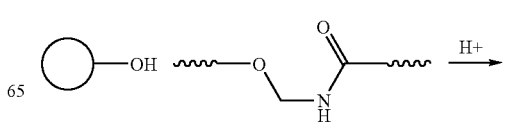

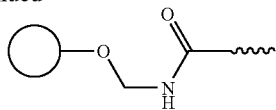

The photoresist composition of the present invention includes a photo-sensitive compound represented by Formula 1, a compound which reacts with a hydroxyl group (—OH) of the compound represented by Formula 1 to combine with the photo-sensitive compound represented by Formula 1 (preferably a compound represented by Formula 2, Formula 3a~3c or Formula 4), a PAG and an organic solvent. Also, at need the photoresist composition of the present invention further includes a base compound as a resist quencher. An amount of the compound represented by Formula 1 is 1~85 weight %, preferably 10~55 weight %. An amount of the compound represented by Formula 2, Formula 3a~3c or Formula 4 which are combined with the compound of Formula 1, is 1~55 weight %, preferably 5~45 weight %. An amount of the PAG is 1~15 weight %, preferably 1~8 weight %. An amount of the organic solvent is 12~97 weight %, preferably 15~95 weight %. An amount of the base compound, if used, is 1~10 weight %, preferably 0.01~2 weight %.

As the PAG, any conventional PAG, which can generate an acid when exposed to light, can be used. The non-limiting examples of the PAG include onium salts, for example sulfonium salts or iodonium salts. Specifically, the PAG is selected from a group consisting of phthalimidotrifluoromethane sulfonate, dinitrobenzyltosylate, n-decyl disulfone and naphthylimido trifluoromethane sulfonate. Also, the PAG is selected from the group consisting of diphenyl iodonium triflate, diphenyl iodonium nonaflate, diphenyl iodonium hexafluorophosphate, diphenyl iodonium hexafluoroarsenate, diphenyl iodonium hexafluoroantimonate, diphenyl p-methoxyphenyl sulfonium triflate, diphenyl p-toluenyl sulfonium triflate, diphenyl p-tert-butylphenyl sulfonium triflate, diphenyl p-isobutylphenyl sulfonium triflate, triphenylsulfonium triflate, tris(p-tert-butylphenyl)sulfonium triflate, diphenyl p-methoxyphenyl sulfonium nonaflate, diphenyl p-toluenyl sulfonium nonaflate, diphenyl p-tert-butylphenyl sulfonium nonaflate, diphenyl p-isobutylphenyl sulfonium nonaflate, triphenylsulfonium nonaflate, tris(p-tert-butylphenyl)sulfonium nonaflate, triphenylsulfonium hexafluoroarsenate, triphenylsulfonium hexafluoroantimonate, triphenylsulfonium triflate and dibutylnaphthylsulfonium triflate. The preferable amount of the PAG is 0.05 to 10 weight parts with respect to 100 weight parts of the photo-sensitive compound. If the amount of the PAG is too little (less than 0.05 weight parts), the light sensitivity of the photoresist composition may decrease. If the amount of the PAG is too much (more than 10 weight parts), the profile of the resist patterns may be deteriorated because the PAG absorbs a lot of ultraviolet rays and a large quantity of acid is produced from the PAG.

The conventional various organic solvents for the photoresist composition can be used as the organic solvent of the photoresist composition of the present invention. Exemplary organic solvent include, but are not limited to, ethyleneglycol monomethylethyl, ethyleneglycol monoethylether, ethyleneglycol monomethylether, ethyleneglycol monoacetate, diethyleneglycol, diethyleneglycol monoethylether, propyleneglycol monomethyletheracetate (PGMEA), propyleneglycol, propyleneglycol, monoacetate, toluene, xylene, methylethylketone, methyl isoamyl ketone, cyclohexanone, dioxane, methyl lactate, ethyl lactate, methyl pyruvate, ethyl pyruvate, methyl methoxy propionate, ethyl ethoxy propionate, N,N-dimethylformamide, N,N-dimethylacetamide, N-methyl 2-pyrrolidone, 3-ethoxy ethyl propionate, 2-heptanone, γ-butyrolactone, ethyl 2-hydroxy propionate, ethyl 2-hydroxy-2-methyl propionate, ethoxyethyl acetate, hydroxyethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and the mixtures thereof. The base compound as the quencher includes tri-ethylamine, tri-iso-butylamine, tri-iso-octylamine, diethanolamine, tri-ethanolamine and mixture thereof.

In order to form a photoresist pattern with the photoresist composition according to the present invention, the following conventional photolithography process can be carried out. First, the photoresist composition is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated (heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol and a surfactant of a proper amount.

Hereinafter, the preferable examples are provided for better understanding of the present invention. However, the present invention is not limited to the following examples.

Synthesis Example 1

Preparation of Photo-Sensitive Compound of Formula 1a

As shown in following Reaction 3, 0.1 mol (15.2 g) of 3,5-dihydroxy acetophenone and 200 ml of tetrahydrofuran (THF) of solvent were added into a 500 ml 2-neck round reaction flask and stirred. After purging dry nitrogen for 30 minutes to completely remove air, the reaction flask was put in the iced water. Leaving the reaction flask in the iced water for 30 minutes, temperature of the reactant was maintained at 0° C. and hydrogen chloride gas was bubbled for 90 minutes. Thereafter the reaction was carried out for 12 hours at room temperature. After completion of the reaction, the solvent was removed under reduced pressure to obtain an intermediate of photo-sensitive compound represented by Formula 1a (Yield: 45%) ($^1$H-NMR: s (7.66, 3H), s (6.51, 6H), s (6.16, 3H), br (5.2, 6H)).

[Reaction 3]

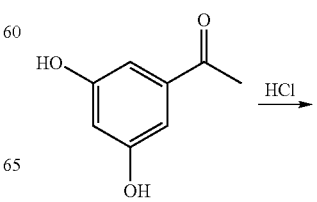

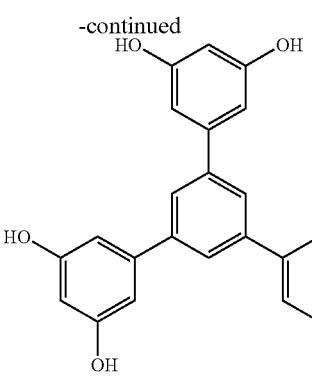

0.01 mol (4.02 g) of the intermediate obtained above and 0.065 mol (7.41 g) of glutaric anhydride were added into 250 ml round flask and 150 ml of toluene was further added to dissolve the intermediate and glutaric anhydride. Thereafter, the reflux reaction was carried out for 12 hours while stirring the reactant under the nitrogen atmosphere. After the completion of the reaction, the solvent was removed and the white-powered photo-sensitive compound of Formula 1a was obtained without additional refining process (Yield: 75%) ($^1$H-NMR: s (7.66, 3H), s (7.1, 6H), s (6.84, 3H), m (2.23, 24H), m (1.83, 12H), br (10.8, 6H)).

Synthesis Example 2

Preparation of Photo-Sensitive Compound of Formula 1b 0.1 mol (13.6 g) of 4-hydroxy acetophenone and 200 ml of tetrahydrofuran (THF) of solvent were added into a 500 ml 2-neck round reaction flask and stirred. After purging dry nitrogen for 30 minutes to completely remove air, the reaction flask was put in the iced water. Leaving the reaction flask in the iced water for 30 minutes, temperature of the reactant was maintained at 0° C. and hydrogen chloride gas was bubbled for 90 minutes. Thereafter the reaction was carried out for 12 hours at room temperature. After completion of the reaction, the solvent was removed under reduced pressure to obtain an intermediate of the photo-sensitive compound represented by Formula 1b (Yield: 55%) ($^1$H-NMR: s (7.6, 3H), s (7.31, 6H), s (6.79, 6H), br (5.0, 3H)).

0.01 mol (3.54 g) of the intermediate obtained in this example and 0.065 mol (7.41 g) of glutaric anhydride were added into 250 ml round flask and 150 ml of toluene was further added to dissolve the intermediate and glutaric anhydride. Thereafter, the reflux reaction was carried out for 12 hours while stirring the reactant under the nitrogen atmosphere. After the completion of the reaction, the solvent was removed and the white-powered photo-sensitive compound of Formula 1b was obtained without additional refining pro-

[Reaction 4]

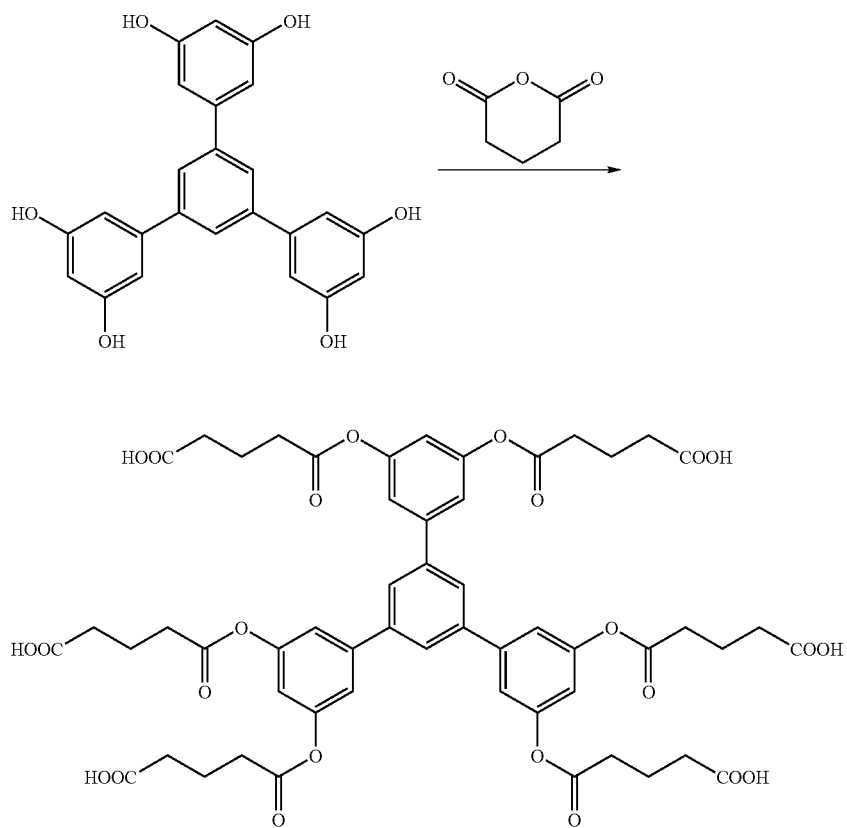

cess (Yield: 78%) ($^1$H-NMR: s (7.66, 3H), s (7.45, 6H), s (7.13, 6H), m (2.23, 12H), m (1.83, 6H), br (11, 3H)).

Synthesis Example 3

Preparation of Photo-Sensitive Compound of Formula 1c

The condensation reaction of 3,5-dihydroxy actophenone was carried out in the same manner as described in Synthesis Example 1 to obtain an intermediate of the photo-sensitive compound represented by Formula 1c (Yield: 55%) ($^1$H-NMR: s (7.6, 3H), s (7.31, 6H), s (6.79, 6H), br (5.0, 3H)).

0.01 mol (4.02 g) of the intermediate obtained in this example and 0.065 mol (14.0 g) of 4-bromomethyl-benzoic acid were added into 250 ml round flask and 150 ml of THF was further added to dissolve the intermediate and 4-bromomethyl-benzoic acid. Thereafter, the reflux reaction was carried out for 12 hours while stirring the reactant under the nitrogen atmosphere. After the completion of the reaction, the resultant was refined through column chromatography method (solvent: ethylacetate/methanol=9/1), to obtain the white-powered photo-sensitive compound of Formula 1c (Yield: 55%) ($^1$H-NMR: s (8.06, 12H), s (7.66, 3H), s (7.4, 12H), s (6.45, 6H), s (6.24, 3H), s (5.2, 12H), br (10.8, 6H)).

Examples 1 to 9

Preparation of Photoresist Composition and Formation of Photoresist Pattern Using the Photoresist Composition The photo-sensitive compound in following Table 1, 100 g of PGMEA as an organic solvent, 4.5 weight % of triphenylsulfonium triflate as a PAG and 2 weight % of trioctylamine as a resist quencher were mixed. The mixture was stirred for 4 hours at room temperature to manufacture a photoresist composition (value of weight % is on the basis of the total composition).

TABLE 1

| | Photo-sensitive compound | | | | | |
| --- | --- | --- | --- | --- | --- | --- |
| | Formula 1a | Formula 1b | Formula 1c | Formula 2f | Formula 3a | Formula 4a |
| Example 1 | 35 g | — | — | 23 g | — | — |
| Example 2 | 35 g | — | — | — | 12 g | — |
| Example 3 | 35 g | — | — | — | — | 5 g |
| Example 4 | — | 47 g | — | 23 g | — | — |
| Example 5 | — | 47 g | — | — | 12 g | — |
| Example 6 | — | 47 g | — | — | — | 5 g |
| Example 7 | — | — | 35 g | 23 g | — | — |
| Example 8 | — | — | 35 g | — | 12 g | — |
| Example 9 | — | — | 35 g | — | — | 5 g |

The photoresist composition manufactured was spin-coated by 3000 Å on a silicon wafer to form a photoresist thin film. Then the photoresist thin film was soft-baked in an oven or heat fan at 130° C. for 90 seconds and then exposed by EUVL (extreme ultraviolet lithography) instrument. Thereafter, the photoresist thin film was again baked at 130° C. for 90 seconds. The baked wafer was dipped in 2.38 wt % TMAH (trimethyl ammonium hydroxide) aqueous solution for 40 seconds for developing to form 32 nm L/S (line/space) pattern. The features of the formed photoresist pattern were measured and the results are shown in following Table 2. The electron microphotograph of the photoresist pattern according to Example 8 is shown in FIG. 1.

TABLE 2

| | Resolution | LER | Coating uniformity | Etching resistance to novolac resin | Scum Control | Profile |
| --- | --- | --- | --- | --- | --- | --- |
| Example 1 | <32 nm | 1.6 nm | 3.2% | 93% | Free | Rectangular |
| Example 2 | <32 nm | 2.0 nm | 4.5% | 95% | Free | Rectangular |
| Example 3 | <32 nm | 1.3 nm | 2.9% | 100% | Free | Rectangular |
| Example 4 | <32 nm | 1.6 nm | 3.7% | 87% | Free | Rectangular |
| Example 5 | <32 nm | 1.4 nm | 4.7% | 91% | Free | Rectangular |
| Example 6 | <32 nm | 2.1 nm | 4.5% | 95% | Free | Rectangular |
| Example 7 | <32 nm | 1.0 nm | 3.5% | 98% | Free | Rectangular |
| Example 8 | <32 nm | 0.9 nm | 2.5% | 105% | Free | Rectangular |
| Example 9 | <32 nm | 2.3 nm | 1.9% | 101% | Free | Rectangular |

In Table 2, the coating uniformity was measured by Nanospec instrument, and the etching resistance is the thickness variation after a dry etching and was measured by Nanospec instrument. Scum and profile were observed by a naked eye. Form Table 2, the photo-sensitive compound and the photoresist composition including the same enable the minimum and uniform pattern formation so that the resolution of the lithography process of less than 32 nm can be made and also line edge roughness (LER) of less than 3 nm (3 sigma) can be controlled. Thus, in case of using the present photo-sensitive compound and the present photoresist composition including the same, the good features of the semiconductor devices can be secured. In addition, since the uniform coating film can be made by the photoresist composition of the present invention, attraction between particles composing the coating film is substantially equal so that non-uniformity of the coating film is less than 3% to get the coating uniformity. Further since amount of benzene ring in the molecule of the photoresist film is much, dry etch resistance of the present photoresist composition is as good as level of novolac resin. The photoresist composition of the present invention reduces scum which is produced from insolubility to the developer and results in an uneven etching.

As described above, the photo-sensitive compound of the present invention has larger than the conventional photo-sensitive polymer in size and well-defined (uniform) structure. Further, the photoresist composition including the photo-sensitive compound not only has excellent coating uniformity, resolution, developing feature and dry etching resistance but also reduces LER.

The invention claimed is:
1. A photo-sensitive compound having a structure of following Formula 1,

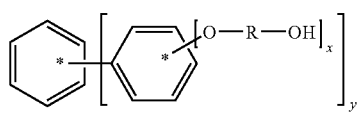

[Formula 1]

wherein in Formula 1, x is an integer of 1 to 5, y is an integer of 2 to 6, and R is a substituted or non-substituted $C_2$~$C_{20}$ hydrocarbon group, and wherein the photo-sensitive compound is selected from the group consisting of

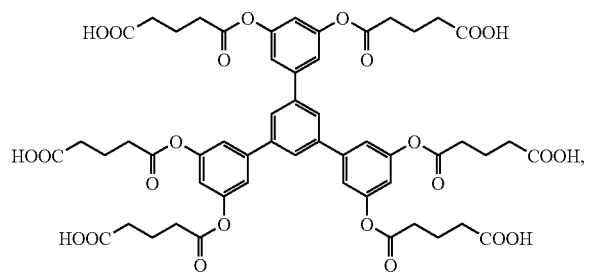

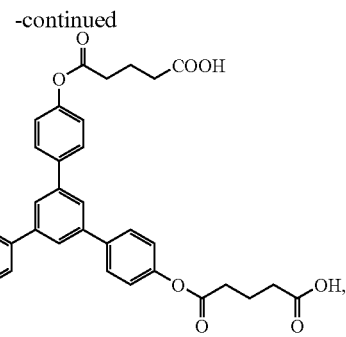

and

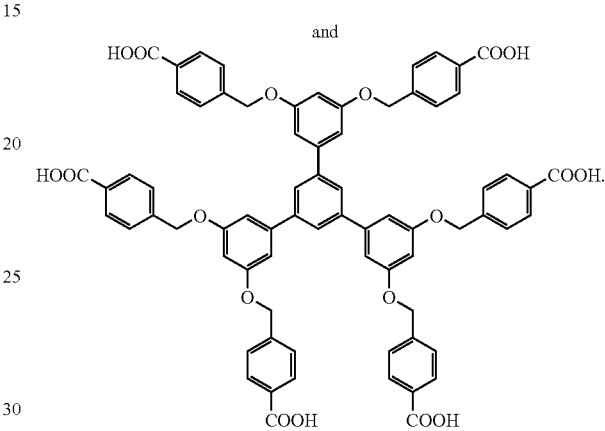

2. A photoresist composition comprising:
1~85 weight % of a photo-sensitive compound represented by following Formula 1, wherein

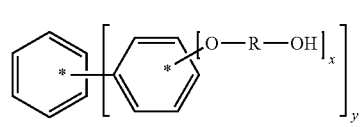

[Formula 1]

in Formula 1, x is an integer of 1 to 5, y is an integer of 2 to 6, R is a substituted or non-substituted $C_2$~$C_{20}$ hydrocarbon group;
1~55 weight % of a compound which reacts with a hydroxyl group (—OH) of the compound represented by Formula 1 to combine with the photo-sensitive compound represented by Formula 1;
1~15 weight % of a photo-acid generator; and
12~97 weight % of an organic solvent.
3. The photoresist composition of claim 2, wherein the compound which combines with the photo-sensitive compound represented by following Formula 1 contains

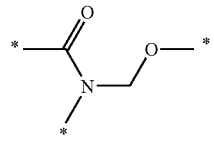

(* indicates a bonding part.).
4. The photoresist composition of claim 2, wherein the compound which combines with the photo-sensitive compound represented by following Formula 1 is a compound represented by following Formula 2, wherein

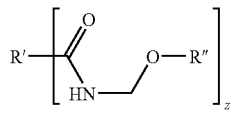

[Formula 2]

in Formula 2, z is an integer of 1 to 20 and R' and R'' are independently a substituted or non-substituted $C_1$~$C_{30}$ hydrocarbon group.

5. A photoresist composition of claim 2, wherein the compound which combines with the photo-sensitive compound represented by following Formula 1 is selected from a group consisting of

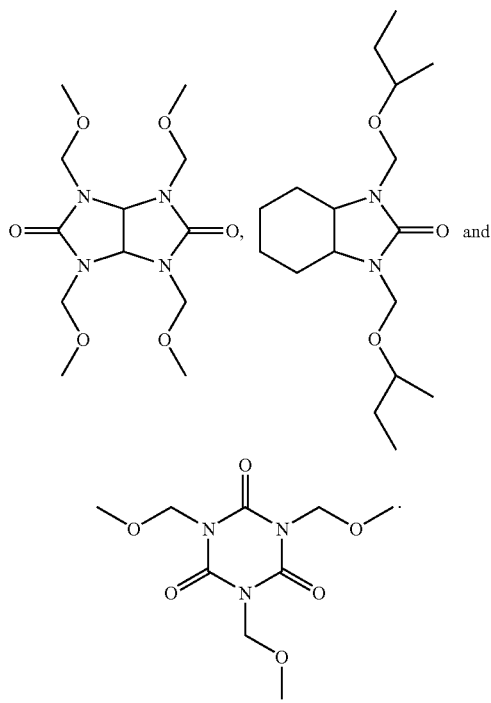

6. A photoresist composition of claim 2, wherein the compound which combines with the photo-sensitive compound represented by following Formula 1 is a compound represented by following Formula 4, wherein

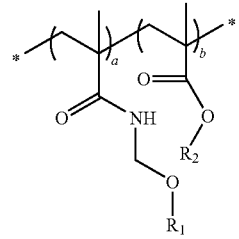

[Formula 4]

in Formula 4, a and b are mole % of respective repeating unit with respect to a total repeating unit of the polymer represented by Formula 4, a and b are 1 to 99 mole % and 1 to 99 mole %, respectively, and $R_1$ and $R_2$ are independently a substituted or non-substituted $C_1$~$C_{30}$ hydrocarbon group.

7. A method for forming a photoresist pattern, comprising the steps of:
   a) coating a photoresist composition on a substrate to form a photoresist layer;
   b) exposing the photoresist layer to a light;
   c) heating the exposed photoresist layer; and
   d) developing the heated photoresist layer to form the photoresist pattern,
   wherein the photoresist composition comprises 1~85 weight % of a photo-sensitive compound represented by following Formula 1, wherein

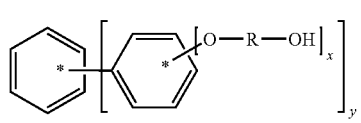

[Formula 1]

in Formula 1, x is an integer of 1 to 5, y is an integer of 2 to 6, R is a substituted or non-substituted $C_2$~$C_{20}$ hydrocarbon group;

1~55 weight % of a compound which reacts with a hydroxyl group (—OH) of the compound represented by Formula 1 to combine with the photo-sensitive compound represented by Formula 1;

1~15 weight % of a photo-acid generator; and

12~97 weight % of an organic solvent.

* * * * *